United States Patent [19]
Abrams et al.

[11] Patent Number: 4,917,243
[45] Date of Patent: Apr. 17, 1990

[54] NEEDLE DISPOSAL DEVICE

[75] Inventors: Stuart G. Abrams, League City; Keith E. Dyer, Galveston, both of Tex.

[73] Assignee: The Board of Regents, University of Texas System, Austin, Tex.

[21] Appl. No.: 232,921

[22] Filed: Aug. 16, 1988

[51] Int. Cl.⁴ .................................... B65D 85/64
[52] U.S. Cl. ........................... 206/365; 29/426.5; 220/1 T; 604/192; 604/263
[58] Field of Search ..................... 206/364–366, 206/438; 29/426.3, 426.5; 220/1 T; 414/786; 604/192, 198, 263

[56] References Cited

U.S. PATENT DOCUMENTS

| | | | |
|---|---|---|---|
| 2,817,434 | 12/1957 | Schmetz et al. | 206/380 |
| 3,207,302 | 9/1965 | Hobbs | 206/366 |
| 4,524,868 | 6/1985 | Buckley et al. | 206/364 |
| 4,627,843 | 12/1986 | Raines | 604/263 |
| 4,631,058 | 12/1986 | Raines | 604/263 |
| 4,643,722 | 2/1987 | Smith, Jr. | 206/365 |
| 4,664,259 | 5/1987 | Landis | 206/365 |
| 4,747,836 | 5/1988 | Luther | 604/263 |

FOREIGN PATENT DOCUMENTS 8800477  1/1988  PCT Int'l Appl. ............ 604/192

Primary Examiner—Jimmy G. Foster
Attorney, Agent, or Firm—Arnold, White & Durkee

[57] ABSTRACT

The present invention provides a device and method for safely conveniently disposing of used needles. Several embodiments are provided. However, in a preferred embodiment, the device will be disposable and will comprise a container for accommodating the needle, said container having a flattened end and upper surface defining an elongated slit widened at one end, said slit shaped to accommodate the needle along its longitudinal axis; at least one resilient flap extending into said slit for retaining the needle in said container; a U-shaped opening disposed in said flattened end and continuous with said slit for separating the needle from a syringe; and a plurality of wings, flanking said slit and extending outwardly from said surface for protecting an individual using the device from accidental contact with the needle.

17 Claims, 3 Drawing Sheets

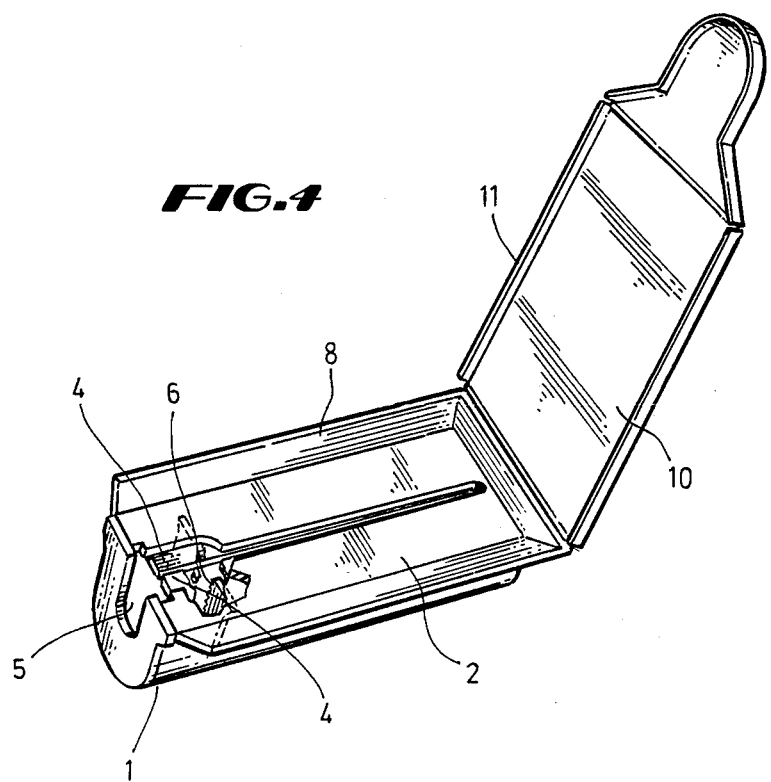
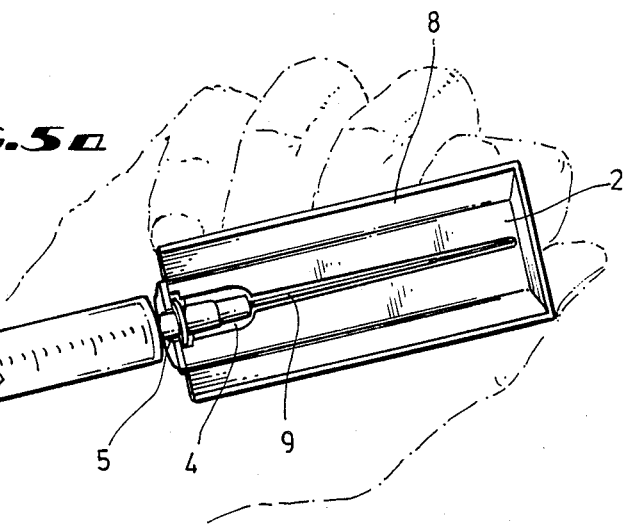

NEEDLE DISPOSAL DEVICE

BACKGROUND OF THE INVENTION

A. Field Of The Invention

This invention relates to the safe disposal of hypodermic needles and, more particularly, to a hand-held container adapted for disposal of hypodermic syringe needles.

B. Description Of The Related Art

Hypodermic needles are widely used in medical examination and treatment facilities for a variety of purposes including, for example, drawing of blood and other bodily fluids, administration of medication, and the like. Most commonly, these needles are individually prepackaged, pre-sterilized, and discarded after a single use. Such disposable needles obviate the need for time consuming re-sterilization and are now used almost exclusively in most major hospitals.

Unfortunately, disposal of such needles has proved problematic. Naked needles may not be placed into a general trash receptacle without compromising the safety of janitorial staff. Moreover, reinsertion of the contaminated needle into its original sheath poses risks that the needle will be mistaken for an unused needle and inadvertently reused. In addition, needles disposed by either of these methods are readily accessible to unauthorized users. Obviously, it is desirable to dispose of the used hypodermic needles in a manner which safely avoids injury to medical personnel caused by inadvertent needle puncture or other contact with a contaminated used needle. Moreover, it is highly desirable to dispose of the used needles in a manner which minimizes risk of unauthorized reuse, for example, by users of illicit drugs. It is also desirable to separate the used hypodermic needle from the syringe barrel in a manner that requires no human contact with the needle itself.

In the past, a variety of devices and systems have been proposed for use in disposing of used hypodermic needles. Examples of such structures can be found in U.S. Pat. No. 4,610,667, issued to Petacino, et al.; U.S. Pat. No. 4,453,648, issued to Harris, et al.; U.S. Pat. No. 4,466,538, issued to Gianni; and U.S. Pat. No. 3,375,849, issued to Hanifl. While such devices have been somewhat useful in providing for safe disposal of contaminated needles, significant room for improvement remains. For example, certain of the devices are mechanically complicated, expensive to manufacture, and not readily disposable. Others are cumbersome and cannot be easily carried or transported from one patient's bedside to another, for example, in a pocket or apron. Moreover, most of these devices require that the needle be inserted "head-on" or "sharp end first," an orientation that is inconvenient, awkward, and significantly increases the user's risk of accidental puncture.

The problems enumerated in the foregoing are not intended to be exhaustive but rather are among many which tend to impair the effectiveness of previously known hypodermic needle disposal devices. Other noteworthy problems may also exist; however, those presented above should be sufficient to demonstrate that needle disposal devices appearing in the art have not been altogether satisfactory.

SUMMARY OF THE INVENTION

It is, therefore, an object of the present invention to provide a novel disposal device for a hypodermic needle which minimizes or reduces the problems of the type previously noted.

It is more particularly an object of the invention to provide a needle disposal device which may be conveniently used by holding the device in the palm of one hand and using the other hand to insert the needle. It is also an object of the present invention to provide a needle disposal device that does not require that the needle be inserted in an awkward and potentially dangerous "head-on" or "sharp end" first orientation.

It is a further object of the invention to provide a needle disposal device which is inexpensively manufactured and readily disposable as well as to provide a device that prevents removal and reuse of a needle contained therein.

It is yet a further object of the invention to provide a device which facilitates insertion of the needle and subsequent separation of the needle from the syringe body without requiring direct manual manipulation of the needle assembly or transport of the naked needle to another location.

It is yet a further object of the invention to provide a device that protects the user from accidental contact with the needle.

Therefore, in a broad and general sense, the present invention addresses one or more of the foregoing by providing a disposal device for a needle comprising a container having an upper surface including an elongated slit shaped to accommodate the needle along its longitudinal axis. In a preferred embodiment, the container will have an elongated semicylindrical shape, for example, a body of a size and shape adapted for comfortable hand held use. For the purpose of the present invention, "semicylindrical" should be construed broadly and includes, for example, U-shaped, V-shaped, and even rounded squared-off containers.

To provide maximal protection to the user, as well as ease of construction and light weight, the container is preferably made of a lightweight material that is resistant to penetration by the needle such as, for example, hard plastic, or the like. Of course, the use of other materials, such as metals or ceramics or the like, is not excluded so long as they serve the function of providing a degree of protection from the needles, as a physical barrier to being penetrated by the needles.

In particular aspects, the disposal device will comprise a retainer means at least partially covering the slit for retaining the needle in the container following use, for example, following removal from the neck of a syringe. In a preferred embodiment, said container means will comprise at least one resilient flap attached along one of its edges, extending adjacent the slit so as to provide a semi-covered slit. Of course, the flap may be attached to the internal or external side of the upper surface of the container. To serve the desired function of sufficient resiliency to maintain the slit in a semi-covered state, as well as to provide a degree of durability, the flap (or flaps) is preferably made of rubber, thin plastic, or the like.

Devices in accordance with the invention will generally comprise a separator for separating the needle from the hypodermic syringe. Such separator will preferably be located at an end of the container that is substantially perpendicular to the upper surface.

In a more preferred embodiment, the separator will comprise a slot that is contiguous with the slit and is of such size and shape that it accommodates the neck of a syringe (the neck is defined herein as the portion of the syringe on which the hub of the needle is mounted) but not the hub of the needle.

An alternative preferred embodiment is adapted for use with threadably mounted or "Leur Lock" type needles. With this embodiment, the separator also includes a plate, disposed within said container substantially parallel to the first end. The plate defines a serrated opening adapted to frictionally grasp a needle hub mounted on the neck of a syringe assembly so as to prevent rotation of the hub when the syringe assembly is rotated.

Of course, it will often be desirable to provide additional protection for an individual using the device from accidental contact with the needle. Therefore, the device may additionally comprise means, extending outwardly from the upper surface of the container, for accomplishing this function. In a more preferred embodiment, the protector will comprise a plurality of wings extending from the upper surface of the container. Preferably, the wings will flank the slit so as to form at least a partial "fence" around the upper surface of the container.

The present invention also provides a device as recited above further comprising a cap for sealing the device. In a more preferred embodiment, the cap will be pivotally mounted on the device.

Accordingly, a highly preferred disposal device for a needle will comprise a container (or housing) for accommodating the needle, said container having an upper surface and an end substantially perpendicular to said upper surface, said upper surface defining an elongated slit widened at one end, said slit shaped to accommodate the needle along its longitudinal axis; at least one resilient flap at least partially covering said slit for retaining the needle in said container; an opening disposed in said end and contiguous with said slit for separating the needle from a syringe; and a plurality of wings extending outwardly from said upper surface so as to form at least a partial fence about said upper surface for protecting an individual using the device from accidental contact with the needle.

In an even more particular embodiment, the device may comprise an elongated container or housing having a first end and a second end and an upper surface substantially perpendicular to said ends. The upper surface includes an elongated axially extending slit, shaped to accommodate a needle along its longitudinal axis so as to allow passage of the needle therethrough. The slit is preferably widened at one end to accommodate the hub of the needle. The device also includes at least one resilient flap which extends into said slit, thereby at least partially covering or closing said slit. The resilient flap serves to retain a needle that has been inserted into the container inside the container. The device also includes a separator for separating the hub of the needle from the neck of the syringe on which the needle hub is mounted. The separator is disposed in the first end of the container and preferably comprises an opening (for example, a V-shaped or U-shaped opening) of such size and shape to accommodate a syringe neck but not a needle hub. The opening is contiguous with the slit. For protecting the fingers of an individual using the device from contact with the needle, the device includes a plurality of protective wings extending outwardly from the slitted upper surface of the container so as to form a partial enclosure or "fence" about the upper surface.

Examples of the more important features of the invention have thus been summarized rather broadly in order that the detailed description thereof that follows may be better understood, and in order that the contribution to the art may be better appreciated. There are, of course, additional features of the invention that will be described hereinafter and which also form the subject of the claims appended hereto. These other objects, features, or advantages of the invention will become apparent with reference to the following detailed description of a preferred embodiment in connection with the accompanying drawings herein like reference numerals have been applied to like elements, in which:

BRIEF DESCRIPTION OF THE DRAWINGS

FIG. 4 shows a device adapted for use with a "Leur-lok" or screw on needle assembly of the flap assembly with covering cap seal shown.

BRIEF DESCRIPTION OF A PREFERRED EMBODIMENT

Figure 1:
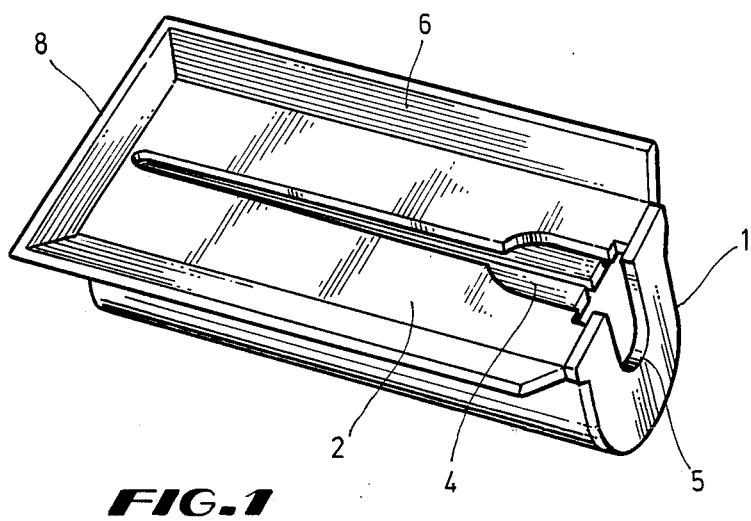
FIG. 1 is a overhead perspective view of a preferred embodiment of the device.

In FIG. 1 there is shown a perspective overhead view of a preferred embodiment of the device of the present invention. In the embodiment shown, the device 1 comprises a container portion 2 for accommodating the syringe needle. The container shown is semicylindrical, or tubular; rectangular containers could also be used. Furthermore, while it is preferred that the container be small enough to be readily held in the hand of the user, larger containers adapted for disposal of a number of needles or for accommodating larger needles may also be manufactured in accordance with the present invention.

Figure 2:
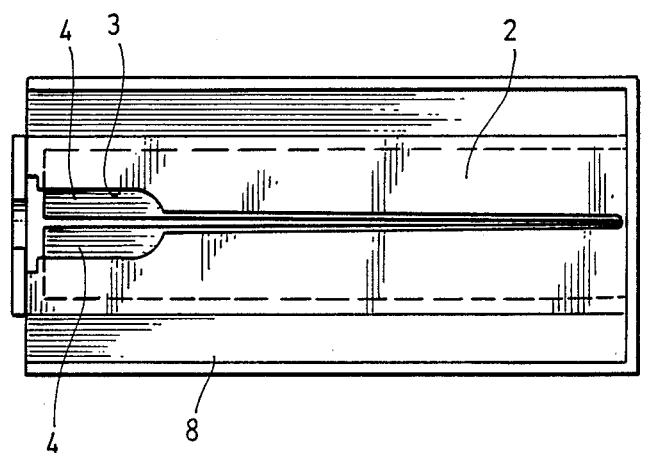
FIG. 2 is a plan view of the device.

An important feature of the present invention is an elongated slit 3 located near the upper surface of the container portion extending along the length of the container portion in an axial direction. In a preferred embodiment, the slit is widened at one end as shown in FIG. 2. Of course, the exact configuration of the slit is not important, so long as it is sufficiently shaped to accommodate the needle along its longitudinal axis. Other slit shapes, for example, a slit formed in the shape of an elongated triangle, are also acceptable. It is, however, preferable to employ a slit that is both wide enough to accept the desired needle size(s), yet narrow enough to prevent removal of the deposited needle from the housing. In a preferred embodiment, the width of the slit is preferably from about 0.05" to about 0.1" and the total length from about 2" to about 2 ¾". Of course, where one desires to use the device for containing needles of larger or smaller than average size, the width and length of the overall slit may be varied accordingly along with that portion (about ⅜" in a preferred embodiment) for the needle hub.

It is also preferred that the device include retainer means for retaining the needle in the container. Preferred retainer means comprise a pair of opposing flaps 4 extending a distance into and thereby partially covering slit 3. It should be apparent to those skilled in the art that a number of suitable constructions for the flap structure may be used. For example, the flaps may be constructed of two separate pieces of material or formed from a single body having a slit therein. Alternatively, the device could comprise a single flap. Various flap configurations may be readily ascertained by those of skill in the art with the aid of the teachings provided by the present disclosure. Preferably, the flap(s) will be made of a resilient material such as rubber, thin plastic, or the like and will be sufficiently flexible to allow insertion of the needle into the container but to prevent its removal therefrom. In a preferred embodiment, the flap or flaps are applied to the underside of the upper surface of the container body, for example, with a suitable adhesive. Alternatively the flaps could be applied to the upper or external side of the container body or could comprise an integral part of the container body, for example, as a thinner portion of the plastic used to form the edges of the slit.

Figure 3:
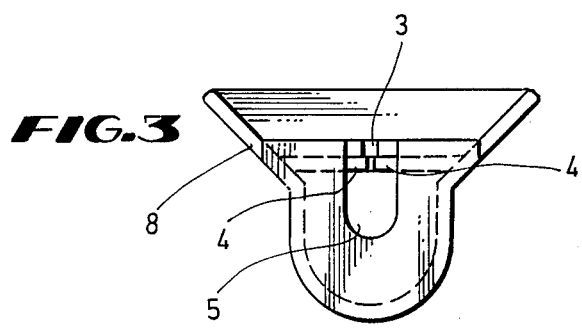
FIG. 3 is a cross-sectional view of a preferred embodiment of the device taken along lines 2—2 of FIG. 2.

Of course, for most uses, it is desirable that the device provide a separator for separating the needle from the neck of the syringe on which it is mounted. In the preferred embodiment, shown in FIG. 3, the separator will comprise a U-shaped slot or opening 5 located in one end of the container. With most syringes, e.g., those having a needle hub frictionally mounted on the syringe neck, the slot should be large enough to accommodate the syringe neck but small enough to preclude the needle hub from passing through the slot. In other words, the slot should be slightly wider than the neck of the syringe, but narrower than the hub of the needle. Of course, other configurations for the slot, for example V-shaped, rectangular, and the like could also be used. Resilient flaps, similar to those described above, may be provided to at least partially cover the slot or opening.

Optionally, as shown in FIG. 4, the device may be adapted for removal and disposal of threadably mounted needles or "Leur Lock" type needle assemblies. With this modification, a mechanism for lockably engaging the needle hub is located inside the body of the container close to the slot in the end of the container. In a preferred embodiment, this mechanism may comprise a plate 6 having a serrated opening 7. The plate 6 is disposed within said container a distance that is sufficiently close to the slot or opening at the end of the container to allow the serrated opening to grasp the hub of the needle when the hub end of the needle is adjacent to the slotted end of the container. This distance will usually be about 10-15 mm, but will vary with the size of the needle. Preferably, the configuration of the serrations is such that one can readily force the needle into the serrated opening but not remove it therefrom. The serrations serve to frictionally grasp the needle hub so as to prevent it from rotating in relation to the serrations when rotational force is applied to the syringe body. Thus, with its hub firmly grasped in the serrated slot, the needle may be disengaged from the syringe by counterclockwise rotation of the syringe assembly.

Finally, as those of skill in the art will recognize, with the "Leur lok" syringe the needle hub is generally mounted within a threaded hood attached to the syringe body. Therefore, when a needle assembly of this type is used, one will need to widen the separator slot accordingly. In other words, with a device adapted for use with the "Leur lok" syringe, the slot should be wide enough to accommodate the threaded hood.

Finally, as discussed above, it is generally important to protect the fingers of the individual using the device from contacting the contaminated needle to be discarded. In the preferred embodiment shown in FIG. 1, this is accomplished by providing a plurality of protective wings 8 flanking the slit and extending outwardly from the upper surface of the container. Preferably, the wings will be integrally connected to the container and will be connected to each other so as to form a "fence" about the upper surface of the container. However, other suitable variations, for example, a device having a pair of opposing wings or a pair of intersecting wings, are also within the scope of the invention. The protective wings may be most readily constructed of the same material used to construct the container, for example, a hard plastic such as polypropylene.

Figure 5B:
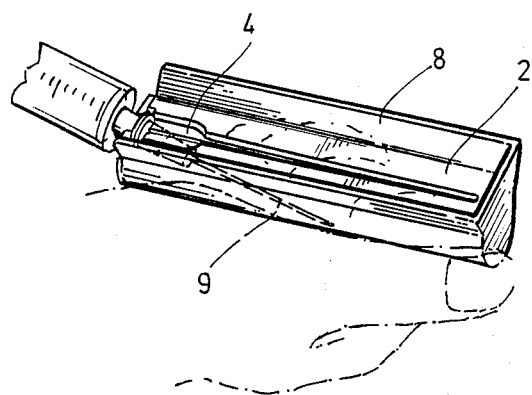
FIG. 5 shows a preferred method for using the device.
Figure 5C:
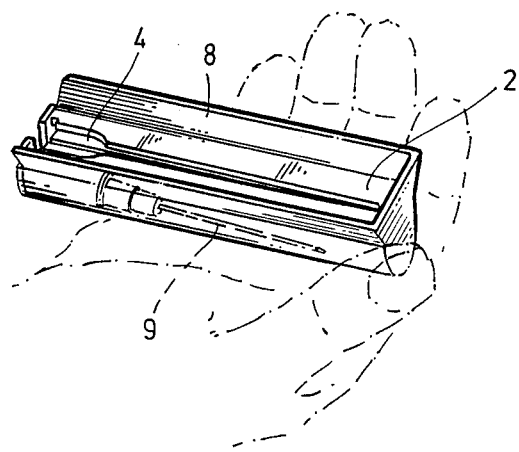

A significant advantage of the present device is the ease with which it may be used. As shown in FIG. 5A, in order to use the preferred embodiment of the device, one simply holds it in the hand with the slitted surface facing upward at a slight angle. The longitudinal axis of the syringe needle 9 is then positioned above the slit in the container in an orientation substantially parallel to the top or upper surface of the container. Of course, with some needles, it may be desirable to angle the tip end of the needle downward slightly, as illustrated in FIG. 5B. The entire needle assembly is then forced downward through the slit, past the resilient flap(s), and into the body of the container. Subsequently, or at the same time, the needle may be separated from the hypodermic syringe.

Of course, the method for separation will vary depending upon the manner in which the needle hub is mounted on the syringe. For a frictionally mounted needle hub/syringe assembly, one simply positions the needle hub so that it abuts the inner surface of the slot at the end of the container and pulls the needle and the container in opposite directions as illustrated in FIG. 5B. Where the needle hub is threadably mounted on the syringe/hub assembly, an embodiment adapted for such a needle may be used. With this embodiment, the needle is inserted into the container so that the hub of the needle is firmly grasped by the serrated slot located near the slotted end of the container. The hypodermic syringe is then rotated and pulled away from the container to disengage the needle hub.

In certain circumstances, it may be desired to provide a device that can be sealed or partially sealed, for example, to prevent leakage of contaminated fluid from the device. In a device having a pair of opposing resilient flaps, the flaps themselves serve this function to a degree. However, in some cases, it will be desirable to apply an additional sealant, preferably in the form of an adhesive plastic tape to the opening 5 in order to seal it. Such adhesive tapes are well known in the art. In situations where the needle may be contaminated with extremely hazardous transmissible agents, it is preferred that the entire device be sealed, including the slitted opening 3. Again, a number of plastic tapes and films may be used for this purpose. Alternatively, the device may be inserted into a second disposal canister thereby doubly ensuring containment of contaminated materials.

Alternatively, a cap may be used for sealing the container. A preferred cap 10, also shown in FIG. 4, will comprise a rectangular first portion corresponding in shape to the "fence" formed by wings 8 and pivotally connected (for example, by an integral hinge), to a second portion shaped to correspond to the slotted end surface of the device. Preferably, the hinge will simply comprise a flexible part of the cap, at which point the cap may be readily folded. A lip 11 extending partially or completely around the perimeter of the cap is adapted to frictionally engage the perimeter of the device thereby allowing the cap to be "snapped on" to the device. Alternatively, the cap may comprise tabs adapted to engage corresponding slots in the body of the device. Finally it should be appreciated that the cap may be pivotally mounted on the upper surface of one of the protective wings, for example by a hinge mechanism similar to that described above.

After the device is used, it may be discarded. Alternatively, it may be reused to dispose of additional needles. However, a single use followed by prompt proper disposal is generally preferred.

It is believed that the device of the present invention may be easily and inexpensively manufactured by any number of techniques generally known to those of skill in the biomedical arts, for example, by pressure injection plastic molding techniques.

To the extent not already indicated, it will also be understood by those of ordinary skill in the art that any one of various specific embodiments herein described and illustrated may be further modified to incorporate features shown in other of the specific embodiments, as desired and other features known to those of skill in the art. The invention in its broader aspects is not limited to the specific embodiments herein shown and described but departures may be made therefrom within the scope of the accompanying claims, without departing from the principles of the invention, and without sacrificing its chief advantage.

What is claimed is:

1. A disposal device for a needle, comprising:
   a container for the needle, said container having at least one surface including an elongated slit shaped to accommodate the needle along its longitudinal axis;
   an end substantially perpendicular to said slitted surface; and
   a separator disposed in said end for separating the needle from a syringe.

2. The device of claim 1 wherein said surface is an upper surface.

3. The device of claim 1, wherein said container has a semicylindrical shape.

4. The device of claim 1, wherein said container is made of a material that is resistant to penetration by the needle.

5. A disposal device for a needle as recited in claim 1, further comprising:
   retainer means at least partially covering said slit for retaining the needle in said container.

6. The device of claim 1, wherein said means comprises a resilient flap, attached along one of its edges, extending adjacent the slit.

7. The device of claim 1, wherein:
   said separator includes a slot, contiguous with said slit, of such shape and size to accommodate a syringe neck.

8. The device of claim 1, wherein:
   said separator includes a slot, contiguous with said slit, of such shape and size to accommodate a syringe neck but not the needle hub.

9. The device of claim 7 wherein the slot is a U-shaped slot.

10. The device of claim 1, further comprising:
    a plate disposed within said container substantially parallel to said end, said plate defining a serrated opening adapted to frictionally grasp a needle hub mounted on a neck of a syringe assembly so as to prevent rotation of the needle hub when the syringe assembly is rotated.

11. A disposal device for a needle as recited in claim 1, further comprising:
    means, extending outwardly from the slitted surface of said container, for protecting an individual using the device from accidental contact with the needle.

12. A disposal device as recited in claim 1, further comprising:
    a plurality of wings, extending from said slitted surface so as to form at least a partial fence about said slitted surface, for protecting an individual using the device from accidental contact with the needle.

13. A disposal device for a needle as recited in claim 1, further comprising:
    a cap for sealing said device.

14. A disposal device for a needle as recited in claim 13, wherein said cap is pivotally mounted on said device.

15. A disposal device for a needle, comprising:
    (a) a container for accommodating the container having an upper surface and an end substantially perpendicular to said upper surface, said upper surface defining an elongated slit widened at one end, said slit shaped to accommodate the needle along its longitudinal axis;
    (b) at least one resilient flap at least partially covering said slit for retaining the needle in said container;
    (c) an opening disposed in said first end and contiguous with said slit for separating the needle from a syringe; and
    (d) a plurality of wings, extending outwardly from said upper surface so as to form at least a partial fence about said upper surface, for protecting an individual using the device from accidental contact with the needle.

16. A method for disposing of a needle mounted on a syringe comprising the steps of:
    (a) providing a container having an upper surface defining an elongated slit shaped to accommodate the needle along its longitudinal axis;
    (b) positioning the needle above said slit so that the longitudinal axis of said needle is substantially parallel to the upper surface of said container;
    (c) forcing the positioned needle through said slit and into said container;
    (d) separating the needle from the syringe so that the needle is retained in the container; and
    (e) disposing of the container.

17. A method for inserting a needle into a needle disposal device comprising the steps of:
    a. providing a container having at least one surface defining an elongated slit;
    b. positioning the needle above said slit so that the longitudinal axis of said needle is substantially parallel to said slitted surface of said container;
    c. forcing the positioned needle through said slit and into said container; and
    d. separating the needle from the syringe so that the needle is retained in the container.

* * * * *

UNITED STATES PATENT AND TRADEMARK OFFICE
CERTIFICATE OF CORRECTION

PATENT NO. : 4,917,243

DATED : April 17, 1990

INVENTOR(S) : Abrams et al.

It is certified that error appears in the above-identified patent and that said Letters Patent is hereby corrected as shown below:

On page 1, number [56]; insert the following references,

| | | |
|---|---|---|
| 4,610,667 | Pedicano et al. | 9/ 1986 |
| 4,453,648 | Harris, et al. | 6/ 1984 |
| 4,466,539 | Frauenhoffer | 8/ 1984 |
| 4,466,538 | Gianni | 8/ 1984 |
| 4,375,849 | Hanifl | 3/ 1983 |
| 4,395,807 | Eldridge, Jr. et al. | 8/ 1983 |
| 4,168,777 | Gaskell, et al. | 9/ 1979 |
| 3,494,201 | Roach | 2/ 1970 |
| 3,329,146 | Waldman, Jr. | 7/ 1967 |
| 3,294,231 | Vanderbeck | 12/ 1966 |
| 2,953,243 | Roehr | 9/ 1960 |

DE 3433359 C   Germany   (1986)

Advertising brochures depicting a number of
    commercially available needle disposal devices.

Signed and Sealed this

Twenty-ninth Day of October, 1991

Attest:

HARRY F. MANBECK, JR.

*Attesting Officer*      *Commissioner of Patents and Trademarks*